United States Patent
Hammond et al.

(10) Patent No.: US 11,255,795 B2
(45) Date of Patent: Feb. 22, 2022

(54) DRIP CHAMBER WITH INTEGRATED OPTICS

(71) Applicants: BAXTER INTERNATIONAL INC., Deerfield, IL (US); BAXTER HEALTHCARE S.A., Glattpark (CH)

(72) Inventors: Peter Hammond, Rochester, NY (US); James F. Munro, Ontario, NY (US); Luke Postema, Webster, NY (US); Tuan Bui, Buffalo, NY (US)

(73) Assignees: BAXTER INTERNATIONAL INC., Deerfield, IL (US); BAXTER HEALTHCARE SA, Glattpark (CH)

( * ) Notice: Subject to any disclaimer, the term of this patent is extended or adjusted under 35 U.S.C. 154(b) by 0 days.

(21) Appl. No.: 16/551,448

(22) Filed: Aug. 26, 2019

(65) Prior Publication Data
US 2019/0376905 A1 Dec. 12, 2019

Related U.S. Application Data

(63) Continuation of application No. 14/872,300, filed on Oct. 1, 2015, now Pat. No. 10,429,312, which is a continuation of application No. 13/829,182, filed on Mar. 14, 2013, now Pat. No. 9,234,850.

(51) Int. Cl.
| | |
|---|---|
| *G01N 21/85* | (2006.01) |
| *H04N 5/225* | (2006.01) |
| *A61M 5/14* | (2006.01) |
| *A61M 5/168* | (2006.01) |

(52) U.S. Cl.
CPC .......... *G01N 21/85* (2013.01); *A61M 5/1411* (2013.01); *A61M 5/1689* (2013.01); *H04N 5/2256* (2013.01); *Y10T 137/0402* (2015.04); *Y10T 137/5762* (2015.04)

(58) Field of Classification Search
None
See application file for complete search history.

(56) References Cited

U.S. PATENT DOCUMENTS

| | | | | |
|---|---|---|---|---|
| 3,800,147 A | * | 3/1974 | Shea | G01N 21/53 250/564 |
| 4,321,461 A | | 3/1982 | Walter, Jr. et al. | |
| 4,328,801 A | | 5/1982 | Marx et al. | |

(Continued)

FOREIGN PATENT DOCUMENTS

| | | |
|---|---|---|
| EP | 0112699 A2 | 4/1984 |
| JP | S61-269020 A | 11/1986 |

(Continued)

OTHER PUBLICATIONS

KR Application No. 10-2015-7028843, Office Action with English translation dated Sep. 1, 2020 (6 pages).

(Continued)

*Primary Examiner* — Talha M Nawaz
(74) *Attorney, Agent, or Firm* — Greer, Burns & Crain, Ltd.

(57) ABSTRACT

A drip chamber for an infusion tube that includes a first end arranged to receive a drip tube, a second end including an exit port, at least one wall connecting the first and second ends, a space enclosed by the first and second ends and the at least one wall, and first and second lenses each directly fixed to said at least one wall.

15 Claims, 6 Drawing Sheets

(56) References Cited

U.S. PATENT DOCUMENTS

| | | | |
|---|---|---|---|
| 4,504,263 A * | 3/1985 | Steuer | A61B 5/208 128/DIG. 13 |
| 4,525,163 A | 6/1985 | Slavik et al. | |
| 4,583,975 A | 4/1986 | Pekkarinen et al. | |
| 4,634,426 A | 1/1987 | Kamen | |
| 4,635,281 A | 1/1987 | Jones | |
| 4,673,820 A | 6/1987 | Kamen | |
| 4,680,977 A * | 7/1987 | Conero | G01F 13/00 356/338 |
| 4,820,281 A | 4/1989 | Lawter, Jr. | |
| 4,909,786 A | 3/1990 | Gijselhart et al. | |
| 4,936,828 A | 6/1990 | Chiang | |
| 5,045,069 A * | 9/1991 | Imparato | A61M 5/1689 604/253 |
| 5,057,090 A | 10/1991 | Bessman | |
| 5,267,980 A * | 12/1993 | Dirr, Jr | A61M 5/1689 128/DIG. 13 |
| 5,411,052 A * | 5/1995 | Murray | A61M 5/1689 137/392 |
| 5,415,641 A | 5/1995 | Yerlikaya et al. | |
| 5,562,615 A | 10/1996 | Nassif | |
| 5,588,963 A | 12/1996 | Roelofs | |
| 5,843,045 A * | 12/1998 | DuPont | A61M 5/1411 604/251 |
| 5,899,665 A | 5/1999 | Makino et al. | |
| 6,049,381 A | 4/2000 | Reintjes et al. | |
| 6,083,206 A | 7/2000 | Molko | |
| 6,149,631 A | 11/2000 | Haydel, Jr. | |
| 6,159,186 A * | 12/2000 | Wickham | A61M 5/1689 604/251 |
| 6,554,791 B1 * | 4/2003 | Cartledge | A61M 1/02 604/131 |
| 6,562,012 B1 | 5/2003 | Brown et al. | |
| 6,736,801 B1 * | 5/2004 | Gallagher | A61M 5/1689 604/251 |
| 6,984,052 B1 * | 1/2006 | Del Castillo | A61M 5/1411 362/101 |
| 7,190,275 B2 | 3/2007 | Goldberg et al. | |
| 7,695,448 B2 | 4/2010 | Cassidy et al. | |
| 7,767,991 B2 | 8/2010 | Sacchetti | |
| 7,892,204 B2 | 2/2011 | Kraus | |
| 7,918,834 B2 | 4/2011 | Memoe et al. | |
| 7,993,399 B2 * | 8/2011 | Peyman | A61F 2/1635 623/6.22 |
| 8,147,447 B2 | 4/2012 | Sundar et al. | |
| 8,622,979 B2 | 1/2014 | Hungerford et al. | |
| 9,234,850 B2 | 1/2016 | Hammond et al. | |
| 9,352,081 B2 | 5/2016 | Munro et al. | |
| 9,476,825 B2 | 10/2016 | Munro | |
| 2003/0045840 A1 | 3/2003 | Burko | |
| 2006/0215053 A1 * | 9/2006 | Kinoshita | G02B 7/08 348/335 |
| 2006/0291211 A1 | 12/2006 | Rodriguez et al. | |
| 2007/0156021 A1 * | 7/2007 | Morse | A61B 1/0019 600/167 |
| 2008/0004574 A1 | 1/2008 | Dyar et al. | |
| 2008/0051732 A1 | 2/2008 | Chen | |
| 2008/0237502 A1 * | 10/2008 | Fago | G21G 4/08 250/506.1 |
| 2008/0252472 A1 * | 10/2008 | Su | A61M 5/1684 340/619 |
| 2010/0309005 A1 * | 12/2010 | Warner | G01F 3/00 340/606 |
| 2012/0013735 A1 * | 1/2012 | Tao | H04N 7/188 348/135 |
| 2012/0095433 A1 * | 4/2012 | Hungerford | A61M 5/1684 604/500 |
| 2013/0085443 A1 * | 4/2013 | Lowery | G01F 1/72 604/65 |
| 2013/0201482 A1 * | 8/2013 | Munro | A61M 5/1689 356/407 |
| 2014/0276457 A1 * | 9/2014 | Munro | A61M 5/1689 604/253 |

FOREIGN PATENT DOCUMENTS

| | | |
|---|---|---|
| JP | H02-286175 A | 11/1990 |
| JP | H04-111353 U | 9/1992 |
| JP | 2002-191692 A | 7/2002 |
| JP | 2002-336350 A | 11/2002 |
| JP | 2011-062371 A | 3/2011 |
| WO | 0123277 A1 | 4/2001 |

OTHER PUBLICATIONS

IN Application No. 9285/DELNP/2015, Examination Report with English translation dated Oct. 27, 2020 (5 pages).

* cited by examiner

DRIP CHAMBER WITH INTEGRATED OPTICS

RELATED APPLICATION

This application is a continuation application of and claims 35 USC 120 priority to U.S. patent application Ser. No. 14/872,300 filed Oct. 1, 2015, which is also a continuation of and claims priority to U.S. patent application Ser. No. 13/829,182 filed Mar. 14, 2013, now U.S. Pat. No. 9,234,850, which is incorporated by reference.

TECHNICAL FIELD

The present disclosure relates to a rectangular drip chamber for an infusion tube with integrated optics, in particular, lenses integrated onto one or more walls of the drip chamber. The present disclosure relates to an optical imaging system including the rectangular drip chamber for the infusion tube with integrated optics.

BACKGROUND

It is known to use lenses, separate from a cylindrical drip chamber, as part of an optical imaging system for an infusion tube. Source light and imaging light must pass through the cylindrical wall of the drip chamber when entering and exiting the drip chamber, respectively, greatly complicating the optical design of both the illumination and imaging sub-systems (lenses, image sensors etc.).

SUMMARY

According to aspects illustrated herein, there is provided a drip chamber for an infusion tube, including: a first end arranged to receive a drip tube; a second end including an exit port; at least one wall connecting the first and second ends; a space enclosed by the first and second ends and the at least one wall; and at least one lens integral to the at least one wall or directly fixed to the at least one wall.

According to aspects illustrated herein, there is provided an optical imaging system for use with an infusion device, including: at least one light source for emitting first light; a drip chamber including at least one wall connecting first and second ends of the drip chamber and a space at least partially enclosed by the at least one wall and the first and second ends; and at least one lens integral to the at least one wall or directly fixed to the at least one wall, the at least one lens arranged to: transmit the first light to the space or receive the first light transmitted through the space. The imaging system includes an optics system including at least one image sensor for receiving the first light from the at least one lens and transmitting data characterizing the first light received from the at least one lens; and at least one specially programmed processor configured to generate, using the data, at least one image of the space.

According to aspects illustrated herein, there is provided a drip chamber for an infusion tube, including: a first end arranged to receive a drip tube; a second end including an exit port; and first, second, third, and fourth walls connecting the first and second ends. In a cross-section orthogonal to a longitudinal axis for the drip tube, the first, second, third, and fourth walls form a rectangle enclosing a space.

According to aspects illustrated herein, there is provided a method of forming a drip chamber for an infusion tube, including: forming a first end arranged to receive a drip tube; forming a second end including an exit port; connecting the first and second ends with at least one wall; enclosing a space with the first and second ends and the at least one wall; and integrating at least one lens into the at least one wall; or directly fixing at least one lens to the at least one wall.

BRIEF DESCRIPTION OF THE DRAWINGS

Various embodiments are disclosed, by way of example only, with reference to the accompanying schematic drawings in which corresponding reference symbols indicate corresponding parts, in which.

DETAILED DESCRIPTION

At the outset, it should be appreciated that like drawing numbers on different drawing views identify identical, or functionally similar, structural elements of the disclosure. It is to be understood that the disclosure as claimed is not limited to the disclosed aspects.

Furthermore, it is understood that this disclosure is not limited to the particular methodology, materials and modifications described and as such may, of course, vary. It is also understood that the terminology used herein is for the purpose of describing particular aspects only, and is not intended to limit the scope of the present disclosure.

Unless defined otherwise, all technical and scientific terms used herein have the same meaning as commonly understood to one of ordinary skill in the art to which this disclosure belongs. It should be understood that any methods, devices or materials similar or equivalent to those described herein can be used in the practice or testing of the disclosure.

Figure 1:
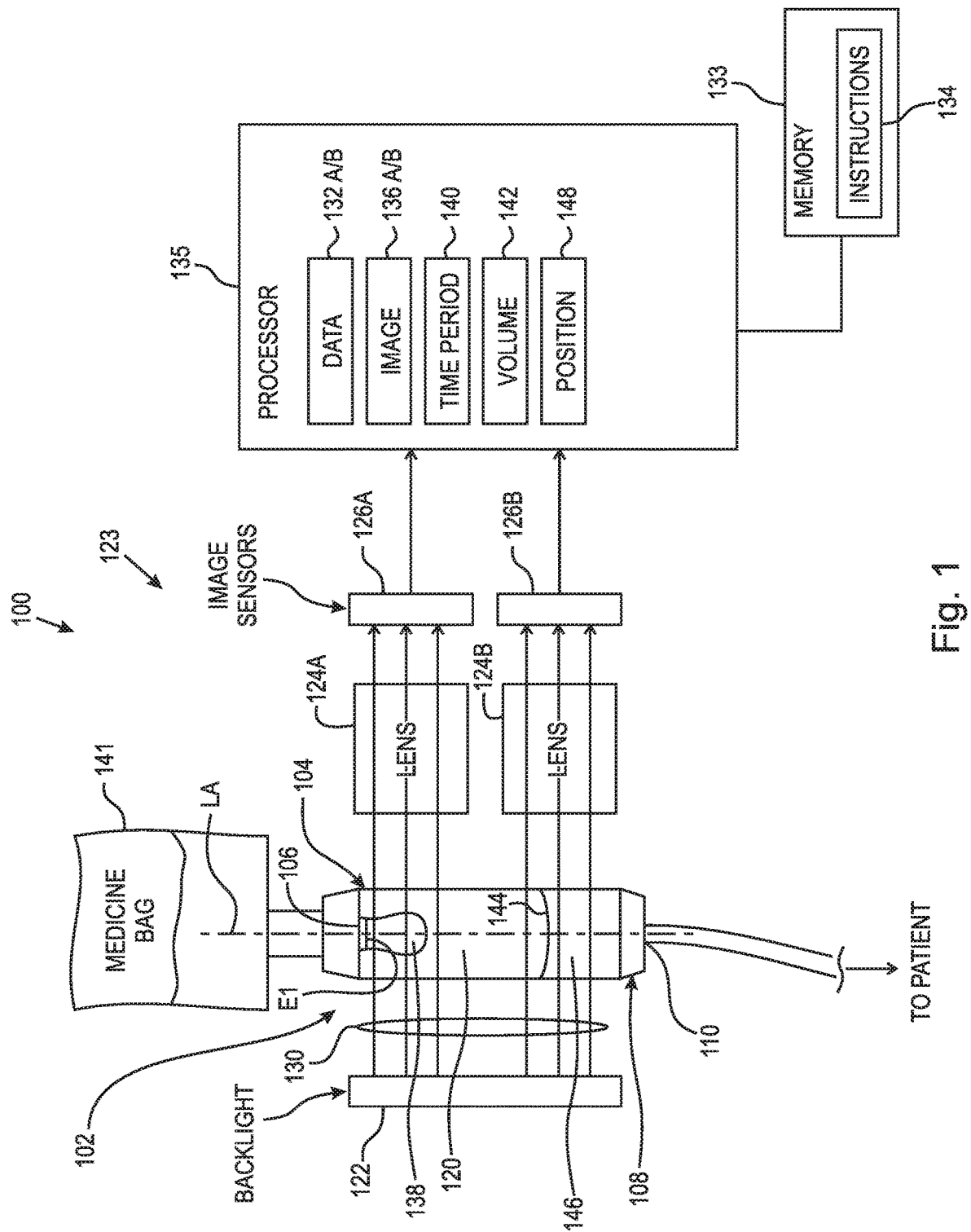
FIG. 1 is a schematic side view of an optical imaging system with a rectangular drip chamber.

FIG. 1 is a schematic side view of optical imaging system 100 with rectangular drip chamber 102.

Figure 2:
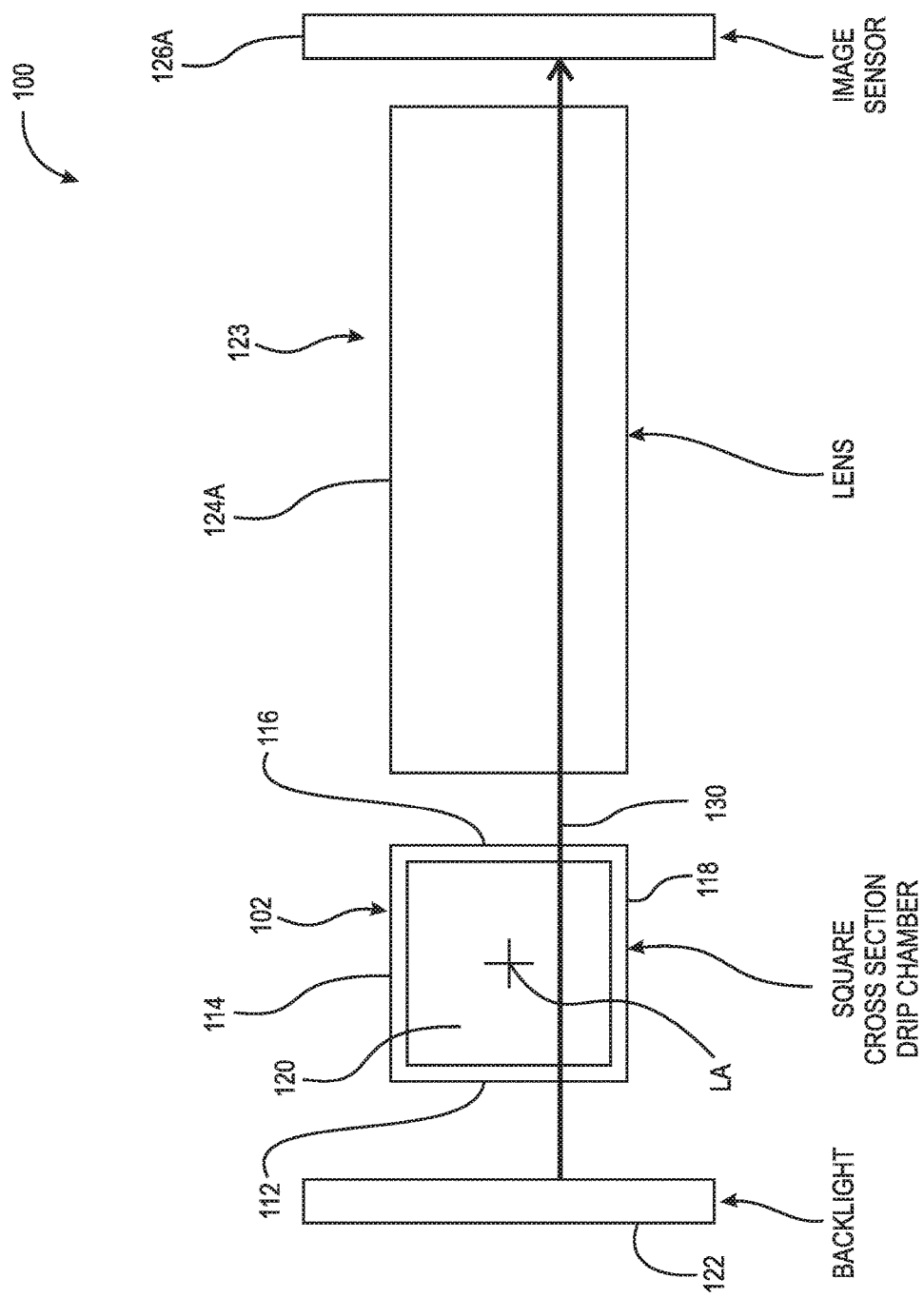
FIG. 2 is a schematic top view of an optical imaging system with a square drip chamber.

FIG. 2 is a schematic top view of optical imaging system 100 with square drip chamber 102. The following should be viewed in light of FIGS. 1 and 2. Chamber 102 includes end 104 arranged to receive drip tube 106 and end 108 including exit port 110. Chamber 102 includes walls 112, 114, 116, and 118 connecting ends 104 and 108 and enclosing space 120. In a cross-section orthogonal to longitudinal axis LA for drip tube 106, for example, as shown in FIG. 2, walls 112, 114, 116, and 118 form a rectangle enclosing space 120. In an example embodiment, the rectangle is a square.

System 100 includes light source 122, and optics system 123 with at least one lens 124 and at least one image sensor 126. In the example of FIGS. 1 and 2, system 123 includes lenses 124A and 124B and image sensors 126A and 126B. The light source is arranged to emit light 130, which is transmitted through space 120 and received by lenses 124A and 124B. Lenses 124A and 124B focus and transmit the light to image sensors 126A and 126B, respectively. Image sensors 126A and 126B receive the light from lenses 124A and 124B, respectively, and generate and transmit data 132 characterizing the light received from lenses 124A and 124B. In the example of FIGS. 1 and 2, sensors 126A and 126B generate and transmit data 132A and 132B, respectively. Memory element 133 is configured to store computer executable instructions 134. Processor 135 is configured to execute instructions 134 to generate, using data 132, at least one image 136 of space 120. In the example of FIGS. 1 and 2, the processor generates images 136A and 136B of space 120 from data 132A and 132B, respectively.

By "characterizing," we mean that the respective data describes, or quantifies, the light, for example, providing parameters enabling generation of an image using the respective data. By "emitting light" we mean that the element in questions generates the light. By "transmitted by" we mean that light passes through the element in question, for example, light emitted by light source 122 passes through space 120.

In an example embodiment, end E1 of drip tube 106 is located in space 120 and image 136A includes end E1. Processor 135 is configured to execute instructions 134 to analyze image 136A to determine if drop 138 is pendant at end E1 and to determine time periods 140 in which drop 138 is or is not pendant at end E1. Time periods 140 can be used to identify when a source of fluid, such as medication bag 141, is empty. In an example embodiment, image 136A includes an image of drop 138 pendant from end E1 and processor 135 is configured to execute instructions 134 to calculate volume 142 of the pendant drop 138, for example, for use in controlling flow through drip chamber 102.

In an example embodiment, meniscus 144 for fluid 146 in drip chamber 102 is located in space 120 and is included in image 136B. Processor 135 is configured to execute instructions 134 to calculate, from image 136B, position 148 of meniscus 144 within drip chamber 102. Position 148 can be used to control flow through drip chamber 102, or if meniscus 144 is determined to be absent, indicating a possible air-in-the-line fault condition, flow through drip chamber 102 can be halted.

In the example of FIGS. 1 and 2, two lenses and two image sensors are used. It should be understood that only one or the other of lens/image sensor pairs 124A/126A or 124B/126B can be used in system 100. It also should be understood that two separate light sources could be used.

Figure 3:
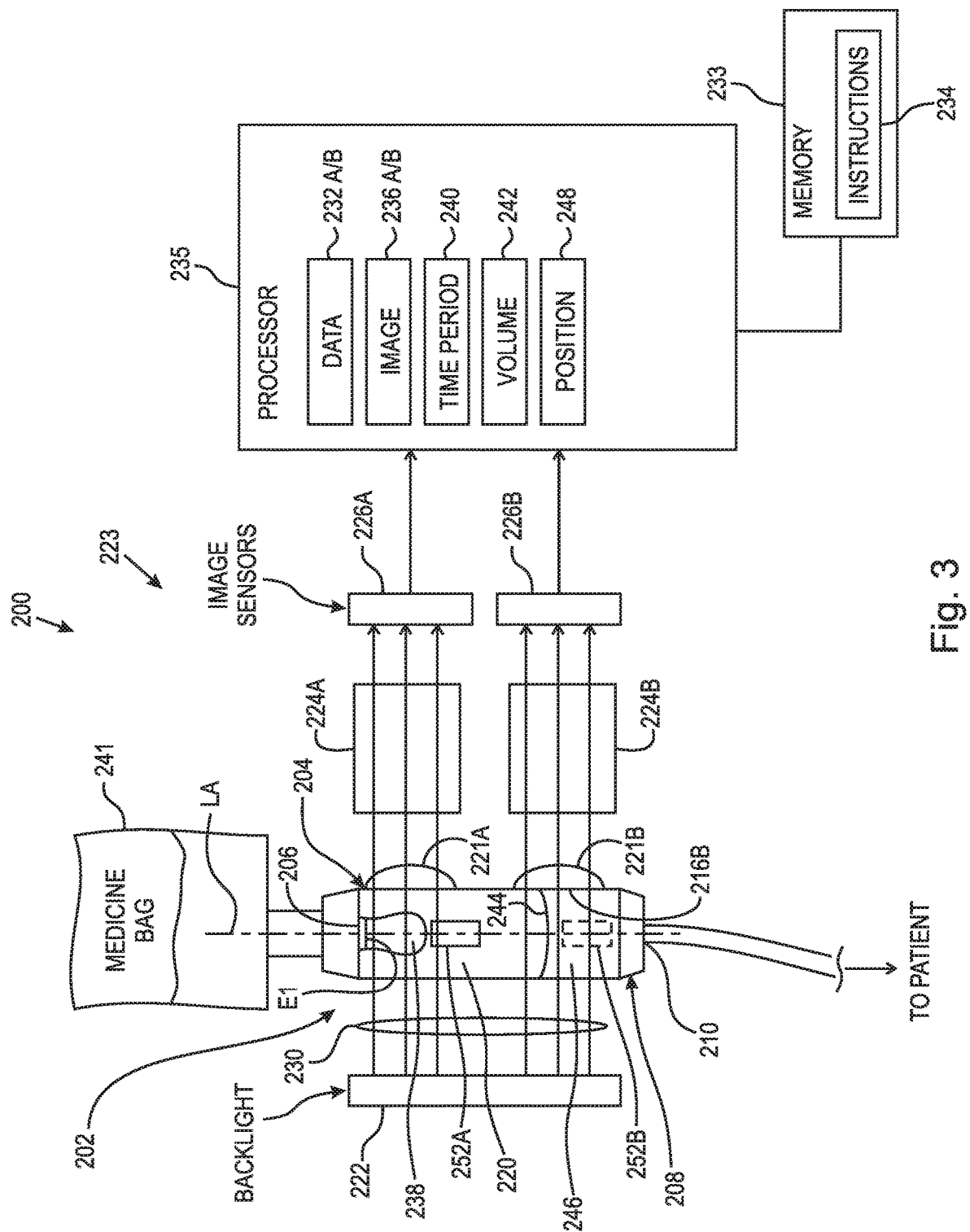
FIG. 3 is a schematic side view of an optical imaging system with a drip chamber including at least one integrated or directly fixed lens.

FIG. 3 is a schematic side view of optical imaging system 200 with drip chamber 202 including at least one integrated or directly fixed lens.

Figure 4:
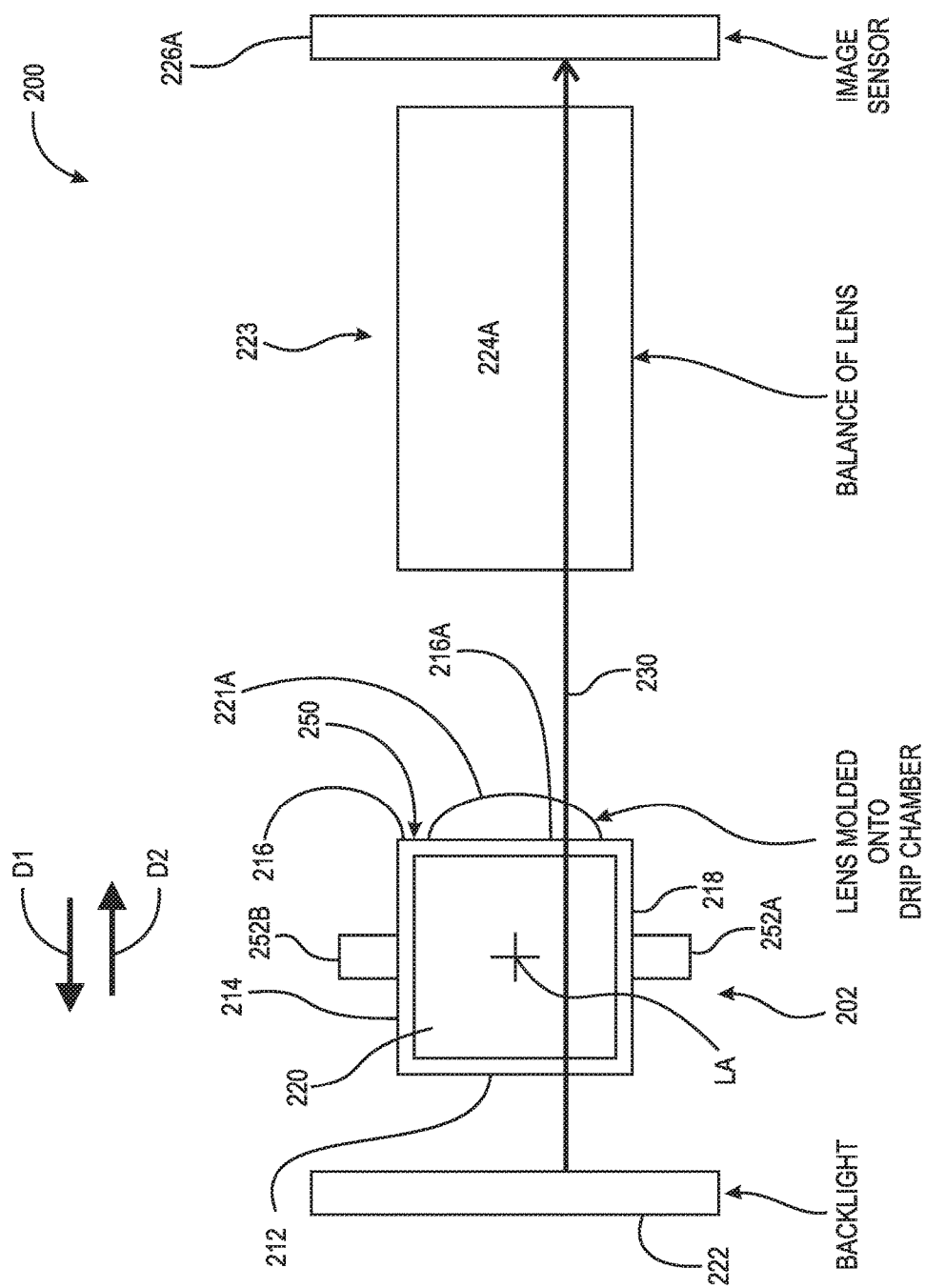
FIG. 4 is a schematic top view of an optical imaging system with a drip chamber including at least one integrated or directly fixed lens.

FIG. 4 is a schematic top view of optical imaging system 200 with drip chamber 202 including at least one integrated or directly fixed lens. The following should be viewed in light of FIGS. 3 and 4. Chamber 202 includes end 204 arranged to receive drip tube 206 and end 208 including exit port 210. Chamber 202 includes walls 212, 214, 216, and 218 connecting second ends 204 and 208 and enclosing space 220. In a cross-section orthogonal to longitudinal axis LA for drip tube 206, for example, as shown in FIG. 4, walls 212, 214, 216, and 218 form a rectangle enclosing space 220. In an example embodiment, the rectangle is a square. Drip chamber 202 includes at least one lens 221 integral to at least one of walls 212, 214, 216, or 218 or directly fixed to at least one of walls 212, 214, 216, or 218, as further described below.

System 200 includes light source 222, and optics system 223 with at least one lens 224 and at least one image sensor 226. In the example of FIGS. 3 and 4, system 223 includes lenses 224A and 224B and image sensors 226A and 226B. The light source is arranged to emit light 230, which is transmitted through space 220 and received by lenses 224A and 224B. Lenses 224A and 224B focus and transmit the light to image sensors 226A and 226B, respectively. Image sensors 226A and 226B receive the light from lenses 224A and 224B, respectively, and generate and transmit data 232 characterizing the light received from lenses 224A and 224B. In the example of FIGS. 3 and 4, sensors 226A and 226B generate and transmit data 232A and 232B, respectively. Memory element 233 is configured to store computer executable instructions 234. Processor 235 is configured to execute instructions 234 to generate, using data 232, at least one image 236 of space 220. In the example of FIGS. 3 and 4, the processor generates images 236A and 236B of space 220 from data 232A and 232B, respectively.

In FIGS. 3 and 4, at least one lens 221 is integral to or directly fixed to wall 212 or 216, for example, and performs functions in addition to those described above. At least one lens 221 is arranged to transmit light 230 to space 220, or receive light 230 transmitted through space 220 and transmit light 230 to lens 224. In the example of FIGS. 3 and 4, lens 221A and 221B are positioned on wall 216 and arranged to receive light 230 transmitted through space 220 and focus and transmit the received light to lens 224A and 224B, respectively.

In an example embodiment, end E1 of drip tube 206 is located in space 220 and image 236A includes end E1. Processor 235 is configured to execute instructions 234 to analyze image 236A to determine if drop 238 is pendant at end E1 and to determine time periods 240 in which drop 238 is or is not pendant at end E1. Time periods 240 can be used to identify when a source of fluid, such as medication bag 241, is empty. In an example embodiment, image 236A includes an image of drop 238 pendant from end E1 and processor 235 is configured to execute instructions 234 to calculate volume 242 of the pendant drop 238, for example, for use in controlling flow through drip chamber 202.

In an example embodiment, meniscus 244 for fluid 246 in drip chamber 202 is located in space 220 and is included in image 236B. Processor 235 is configured to execute instructions 234 to calculate, from image 236B, position 248 of meniscus 244 within drip chamber 202. Position 248 can be used to control flow through drip chamber 202, or if meniscus 244 is determined to be absent, indicating a possible air-in-the-line fault condition, flow through drip chamber 202 can be halted.

In the example of FIGS. 3 and 4, two lenses 224 and two image sensors are used. It should be understood that only one or the other of lens/image sensor pairs 224A/226A or 224B/226B can be used in system 100. It also should be understood that two separate light sources could be used to emit light. In the example of FIGS. 3 and 4, lenses 221A and 221B are shown; however, it should be understood that drip chamber 202 can be equipped only one or the other of lenses 221A or 221B.

In an example embodiment, the portion of the wall to which lenses 221A and 221B are integral or attached, for example, portions 216A and 216B of wall 216, are flat. For example, wall 216 includes exterior surface 250 with flat portions 216A and 216B and lenses 221A or 221B are integral to flat portions 216A and 216B or directly fixed to flat portions 216A and 216B. In an example embodiment, walls 212 and 216 are flat, substantially parallel to each other, and face in directions D1 and D2, respectively. In an example embodiment, portions 216A and 216B and at least portions of wall 212 aligned with portions 216A and 216B, orthogonal to longitudinal axis LA for the drip chamber, are flat and substantially parallel to each other, for example, along longitudinal axis LA. That is, light 230 passing through lenses 221A and 221B passes through flat and substantially parallel portions of wall 212.

Although walls 214 and 218 are shown as flat forming a square with walls 212 and 216 in FIG. 4, it should be understood that walls 214 and 218 are not required to have any particular shape or to form any particular shape of space 220. It also should be understood that although walls 212 and 216 are shown as flat, the portion of wall 216 not including portions 216A and 216B, and the portions of wall 212 not aligned with portions 216A and 216B orthogonal to longitudinal axis LA, are not required to have any particular shape.

It should be understood that lens 221A and/or 221B can be positioned on wall 212, in which case, the above discussion regarding wall 216 and wall 212 with portions 216A and 216B and lenses 221A and 221B is applicable to wall 212 and wall 216 having the lenses and flat portions. It also should be understood that only one of lenses 221A or 221B can be positioned on drip chamber 202, either on wall 212 or on wall 216. The single lens 221 can be positioned to transmit light to image the drip tube or to transmit light to image the meniscus.

Figure 5:
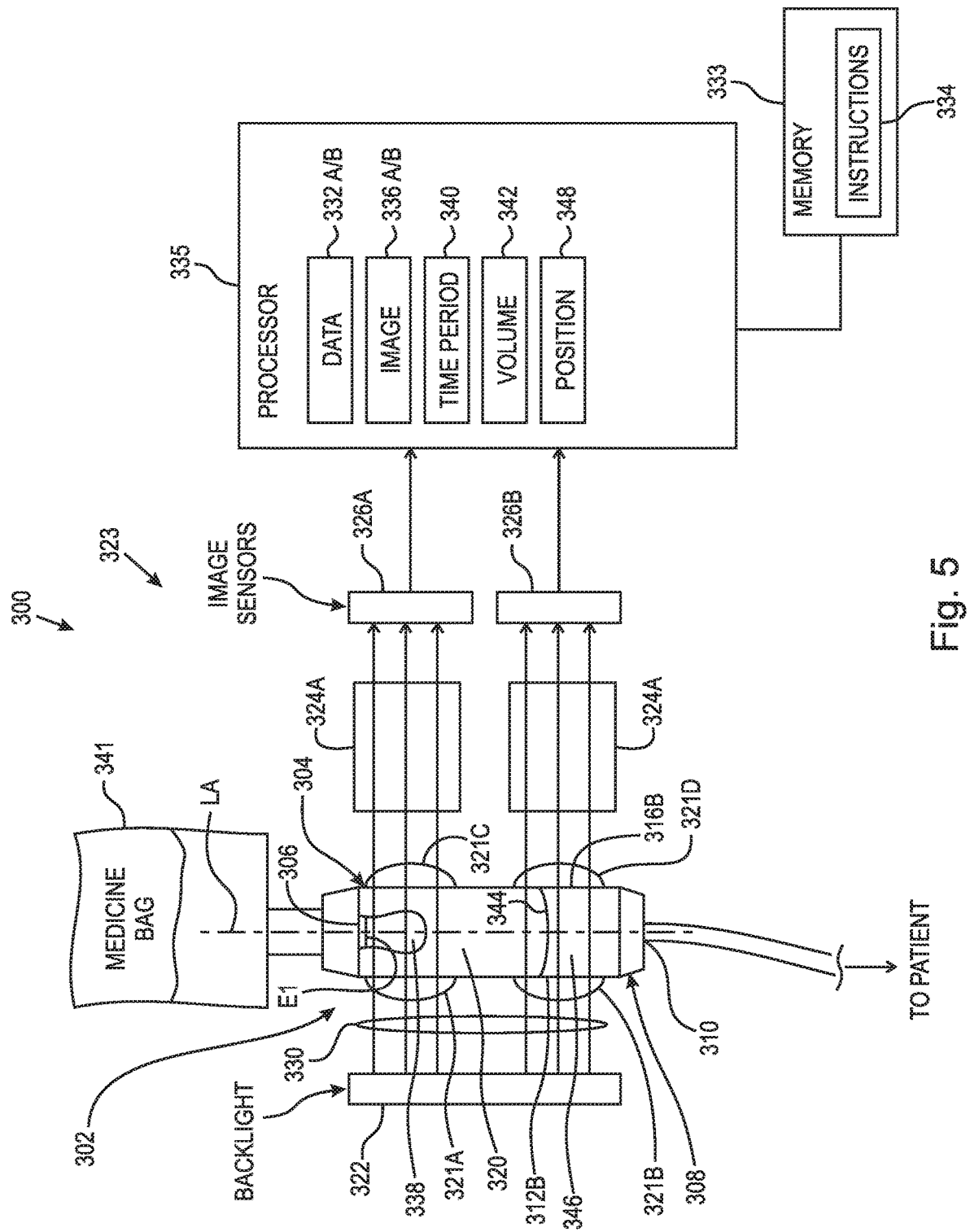
FIG. 5 is a schematic side view of an optical imaging system with a drip chamber including at least one integrated or directly fixed lens.

FIG. 5 is a schematic side view of optical imaging system 300 with drip chamber 302 including at least one integrated or directly fixed lens.

Figure 6:
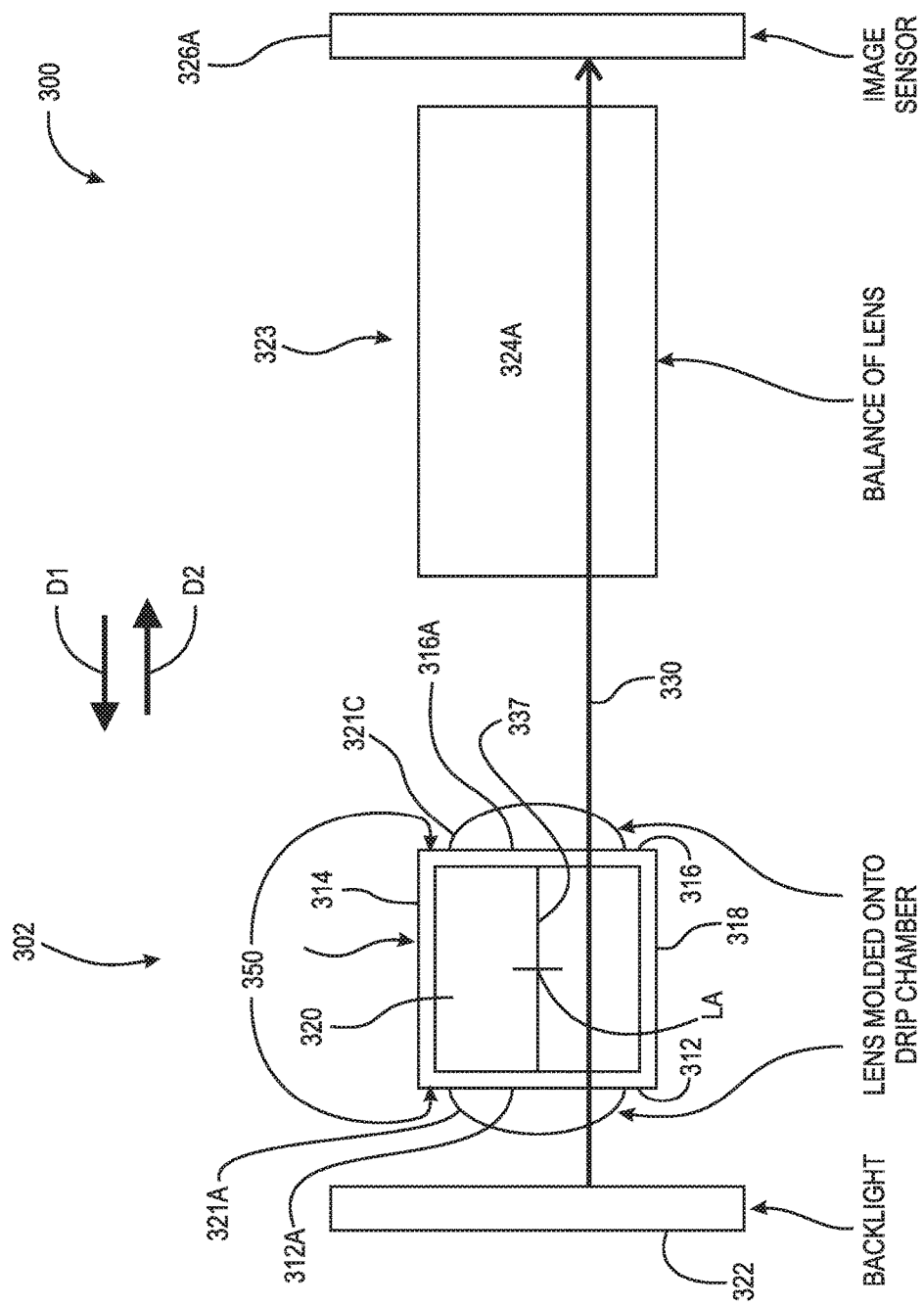
FIG. 6 is a schematic top view of an optical imaging system including at least one integrated or directly fixed lens.

FIG. 6 is a schematic top view of optical imaging system 300 with drip chamber 302 including at least one integrated or directly fixed lens. The following should be viewed in light of FIGS. 5 and 6. Chamber 302 includes end 304 arranged to receive drip tube 306 and end 308 including exit port 310. Chamber 302 includes walls 312, 314, 316, and 318 connecting ends 304 and 308 and enclosing space 320. In a cross-section orthogonal to longitudinal axis LA for drip tube 306, for example, as shown in FIG. 6, walls 312, 314, 316, and 318 form a rectangle enclosing space 320. In an example embodiment, the rectangle is a square. Drip chamber 302 includes at least two lenses 321 integral to walls 312 and 318, or directly fixed to walls 312 and 318, as further described below. In general, lenses 321 are in pairs (one on side 312 and the other on side 316) aligned with a line orthogonal to axis LA. In FIGS. 5 and 6, two pairs of lenses, 321A/C and 321B/D are shown.

System 300 includes light source 322, and optics system 323 with at least one lens 324 and at least one image sensor 326. In the example of FIGS. 5 and 6, system 323 includes lenses 324A and 324B and image sensors 326A and 326B. The light source is arranged to emit light 330, which is transmitted through space 320 and received by lenses 324A and 324B. Lenses 324A and 324B focus and transmit the light to image sensors 326A and 326B, respectively. Image sensors 326A and 326B receive the light from lenses 324A and 324B, respectively, and generate and transmit data 332 characterizing the light received from lenses 324A and 324B. In the example of FIGS. 5 and 6, sensors 326A and 326B generate and transmit data 332A and 332B, respectively. Memory element 333 is configured to store computer executable instructions 334. Processor 335 is configured to execute instructions 334 to generate, using data 332, at least one image 336 of space 320. In the example of FIGS. 5 and 6, the processor generates images 336A and 336B of space 320 from data 332A and 332B, respectively.

In FIGS. 5 and 6, lenses 321 are integral to or directly fixed to walls 312 and 316 and perform functions in addition to those described above. Pairs of lenses 321 are arranged to transmit light 330 to space 320, and receive light 330 transmitted through space 320. In the example of FIGS. 5 and 6, lens 321A and 321C are arranged to receive light 330 from source 322 and transmit light 330 through space 320; and lenses 321B and 321D are arranged to receive light 330 transmitted through space 320 and focus and transmit the received light 320. Thus, lenses 321A and 321C form a pair (the same light passes through both lenses) and lenses 321B and 321D form a pair (the same light passes through both lenses). As shown in FIG. 6, axis LA is located between lenses 321A and 321C and lenses 321B and 321D along plane 337 orthogonal to axis LA.

In an example embodiment, end E1 of drip tube 306 is located in space 320 and image 336A includes end E1. Processor 335 is configured to execute instructions 334 to analyze image 336A to determine if drop 338 is pendant at end E1 and to determine time periods 340 in which drop 338 is or is not pendant at end E1. Time periods 340 can be used to identify when a source of fluid, such as medication bag 341, is empty. In an example embodiment, image 336A includes an image of drop 338 pendant from end E1 and processor 335 is configured to execute instructions 334 to calculate volume 342 of the pendant drop 338, for example, for use in controlling flow through drip chamber 302.

In an example embodiment, meniscus 344 for fluid 346 in drip chamber 302 is located in space 320 and is included in image 336B. Processor 335 is configured to execute instructions 334 to calculate, from image 336B, position 348 of meniscus 344 within drip chamber 302. Position 348 can be used to control flow through drip chamber 302, or if meniscus 344 is determined to be absent, indicating a possible air-in-the-line fault condition, flow through drip chamber 302 can be halted.

In the example of FIGS. 5 and 6, two lenses 324 and two image sensors are used. It should be understood that only one or the other of lens/image sensor pairs 324A/326A or 324B/326B can be used in system 300. It also should be understood that two separate light sources could be used to emit light. In the example of FIGS. 5 and 6, lenses 321A-D are shown; however, it should be understood that drip chamber 302 can be equipped only one or the other of pair of lenses 321A/C or 321B/D.

In an example embodiment, the portions of the walls to which lenses 321A-D are integral or attached, for example, portions 312A and 312B of wall 312, and portions 316A and 316B of wall 316 are flat. For example, walls 312 and 316 include respective exterior surfaces 350 with flat portions 312A and 312B and flat portions 316A and 316B, respectively. Lenses 321A and 321B are integral to portions 312A and 312B or directly fixed to portions 312A and 312B, respectively; and lenses 321C and 321D are integral to portions 316A and 316B or directly fixed to portions 316A and 316B, respectively. Portions 312A and 316A are substantially parallel to each other and portions 312B and 316B are substantially parallel to each other. In an example embodiment, walls 312 and 316 are flat and face in directions D1 and D2, respectively. In an example embodiment, walls 312 and 316 are flat and substantially parallel to each other, for example, substantially parallel to longitudinal axis LA for the drip chamber. Although walls 314 and 318 are shown as flat and forming a square with walls 312 and 316 in FIG. 6, it should be understood that walls 314 and 318 are not required to have any particular shape or to form any particular shape of space 320. It also should be understood that although walls 312 and 316 are shown as flat, the portions of wall 312 not including portions 312A and 312B, and the portions of wall 316 not including portions 316A and 316B, are not required to have any particular shape.

Advantageously, flat walls for drip chamber 102, 202, or 302, for example, flat walls 112 and 116 for drip chamber 102, eliminate the problem noted above of source light and imaging light passing through a cylindrical wall of a drip chamber when entering and exiting the drip chamber. Thus, the optical design of both an illumination system, for example, light sources 122, 222, or 322, and an optical system such as system 123, 223, or 323, including components such as lenses 124, 224, or 324 and/or imagers 126, 226, or 326, can be advantageously simplified, reducing complexity and cost of systems 100, 200, and 300. For example, drip chamber 302 with a substantially parallel portions 312A/316A and 312B/316B reduces optical aberrations such as distortion, astigmatism, and coma.

Integrally molding lens or lenses 221/321 to drip tubes 206/306, or attaching lens or lenses 221/321 directly to drip tubes 206/306, advantageously enables faster speeds for lens or lenses 221/321, without compromising the performance of lens or lenses 221/321 in other areas. Integrally molding lens or lenses 221/321 to drip tubes 206/306, or attaching lens or lenses 221/321 directly to drip tubes 206/306 also reduces the parts count, cost, and complexity of systems 200/300. Further, lens or lenses 221/321 enable a reduction in the distance between a backlight such as sources 222/323 and an image sensor such as 226/326, advantageously reducing a size of an infusion pump including drip chamber 202 or 302.

Installing lens or lenses 221/321 provides an extra degree of freedom in the design of illumination for system 200/300, for example, enabling greater control over spatial and angular flux incident on a pendant drop being illuminated.

It should be understood that any combination of the drip chamber configurations shown in FIGS. 1 through 6 can be used in a single drip chamber. For example, drip chamber 202 or 302 can include lens/sensor pair 221A/224A/226A and lenses/sensor grouping 321B/321D/324B/326B. For example, drip chamber 200 or 300 can include lens/sensor grouping 221B/224B/226B and lenses/sensor pair 321A/321C/324A/326A.

Light sources 122, 222, and 322 can be different from each other and can be any light source known in the art, including, but not limited to a light-emitting diode (LED), an array of LEDs, a laser diode, an incandescent lamp, or a fluorescent lamp.

The following provides further detail regarding drip chambers 102, 202, and 302 and/or lenses 221/321. Lenses 221/321 can be any combination of: positive or negative; spherical or aspherical; rotationally symmetric or asymmetric; or cylindrical. Lens or lenses 221/321 can be Fresnel lenses. Lens or lenses 221/321 can have a diffractive optical element installed onto them or can be replaced by a diffractive optical element. Drip chamber 202/302 with integral lens or lenses 221/321 can be fabricated by injection molding. Drip chamber 202/302 with integral lens or lenses 221/321 can be made from a polymer, such as acrylic, polycarbonate, or polystyrene. A cross-section of drip chambers 102, 202, or 302 can be circular, elliptical, rectangular, square, or rectangular with radiused corners.

In an example embodiment, drip chamber 202 or 302 includes installation feature 252 so that the drip chamber can be installed in an infusion pump in only one (desired) way, for example, so that lens or lenses 221 or 321 are properly oriented. In an example embodiment, drip chamber 202 or 302 includes an alignment feature to ensure that when installed, an optical axis of the drip chamber is co-linear with an axis of lens or lenses, such as lens or lenses 221 or 321, and/or the axis of a light source such as light source 222 or 322 The installation and alignment features can be combined.

Lens or lenses 221 or 321 can be partially recessed into the walls of drip chamber 202 or 302 so that the overall thickness of the walls are not significantly increased as the thickest part of lens or lenses 221 or 321. Such a configuration can avoid "sinks" and improve the surface figure of the lens in question.

In an example embodiment, drip chamber 202 includes installation features, such as features 252A and/or 252B. Features 252A and 252B are used to precisely locate lenses 221A and 221B, respectively, on respective optical axis. The size, shape, and location of features 252A and/or 252B are for purposes of illustration only, other sizes, shapes, and locations are possible. The preceding discussion also is applicable to drip chamber 302.

Lens or lenses 221 or 321 can be produced as part of the molding process for drip chamber 202 or 302, or can be fabricated in separate molding processes and subsequently bonded to chamber 202 or 302. The bonding can be executed with adhesive or through an ultrasonic or thermal bonding process. The respective prescriptions of lens or lenses 221 or 321 can be different, resulting in different imager magnifications. The different magnifications can be matched to various configurations of chamber 202 or 302 to enhance operations such a imaging of drops pendant from drip tube 208 or 308. Interlock-like features can be integrally molded onto drip chamber 202 or 302, which can be sensed by an infusion pump, causing the pump to utilize different calibration flow-rate constant according to the sensed magnification. A two-dimensional bar code, such as QR code, can be installed onto a surface of drip chamber 202 or 302 within the field of view of the imager (but not blocking view of areas of interest such as drip tube 208, or 308). The code can include information regarding drip chamber 202 or 302 such as: manufacturer, date of manufacture, authentication information, magnification, nominal drip rate of a nozzle.

It will be appreciated that various of the above-disclosed and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

What is claimed is:

1. A drip chamber for an infusion tube, comprising:
a first end arranged to receive a drip tube;
a second end including an exit port;
at least one wall connecting the first and second ends;
a space enclosed by the first and second ends and the at least one wall;
at least one lens being directly fixed to an outer surface of said at least one wall and having a curved surface facing away from said at least one wall, said at least one lens having a curvature that is different than a curvature of said outer surface of said at least one wall, and said at least one lens configured for receiving light transmitted through the space and focusing and transmitting the light to another lens.

2. The drip chamber of claim 1, further comprising first and second walls, respectively, substantially parallel to each other, wherein said at least one lens is directly fixed to only one of the first or second walls.

3. The drip chamber of claim 1, wherein the at least one wall forms a rectangle enclosing the space in a cross-section orthogonal to a longitudinal axis of the drip chamber.

4. The drip chamber of claim 1, further comprising a first wall and a second wall, respectively, the first lens is directly fixed to the first wall and the second lens is directly fixed to the second wall.

5. The drip chamber of claim 1, wherein said at least one lens includes a flat surface and an opposing curved surface.

6. An optical imaging system for use with an infusion device, comprising:
   at least one light source for emitting first light;
   a drip chamber including first and second walls connecting first and second ends of the drip chamber, a space at least partially enclosed by the first and second walls and the first and second ends, a drip tube including an end that is located in the space, and at least one lens, said at least one lens being fixed directly to an outer surface of one of said first and second walls and including a curved surface facing away from said one of said first and second walls, said at least one lens being on a side of said drip chamber that is opposite to said at least one light source, said at least one lens being arranged to transmit the first light to the space or receive the first light transmitted through the space; and
   an optics system including at least one image sensor for receiving the first light from said at least one lens and transmitting data characterizing the first light received from said at least one lens.

7. The optical imaging system of claim 6, wherein the at least one wall includes an exterior surface and said at least one lens is directly fixed to the exterior surface.

8. The optical imaging system of claim 6, wherein said at least one lens includes first and second lenses, the first lens is arranged to transmit the first light to the space and the second lens is arranged to receive the first light transmitted by the first lens through the space and transmit the received first light to the at least one image sensor.

9. The optical imaging system of claim 6, wherein a meniscus for fluid in the drip chamber is located in the space and at least one specially programmed processor is configured to calculate, from the at least one image, a position of the meniscus within the drip chamber.

10. The optical imaging system of claim 6, wherein said at least one lens includes a flat surface and an opposing surface, wherein said opposing surface is said curved surface.

11. A drip chamber for an infusion tube, comprising:
    a first end including a drip tube;
    a second end including an exit port;
    first, second, third, and fourth walls connecting the first and second ends, wherein, in a cross-section orthogonal to a longitudinal axis of the drip tube, and form a rectangle enclosing a space;
    a drip tube including an end located in the space; and
    at least one lens directly fixed to an outer surface of one of said first, second, third and fourth flat portions of said first, second, third and fourth walls, said at least one lens including a curved surface that faces away from said one of said first, second, third and fourth walls.

12. The drip chamber of claim 11, wherein the at least one lens includes a flat surface and an opposing surface, wherein said opposing surface is said curved surface.

13. A method of forming a drip chamber for an infusion tube, the method comprising:
    forming a first end arranged to receive a drip tube;
    forming a second end including an exit port;
    connecting the first and second ends with at least one wall and enclosing a space with the first and second ends and the at least one wall;
    providing at least one lens having a curved surface; and
    directly fixing said at least one lens to an outer surface of the at least one wall, said curved surface facing way from the at least one wall, wherein a curvature of said at least one lens is different than a curvature of said outer surface of said at least one wall.

14. The method of claim 13, further comprising generating at least one image of the space, wherein the at least one image includes an image of a drop pendant from the end of the drip tube.

15. The method of claim 14, further comprising calculating a volume of the pendant drop from the image of the drop pendant.

* * * * *